United States Patent
Ramanthan et al.

(10) Patent No.: US 6,358,509 B1
(45) Date of Patent: Mar. 19, 2002

(54) ANTIBODY ANTAGONISTS OF HUMAN INTERLEUKIN-4

(75) Inventors: Lata Ramanthan, West Orange; Gail F. Seelig, Watchung; Paul P. Trotta, Rutherford, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 08/271,539

(22) Filed: Jul. 7, 1994

Related U.S. Application Data

(63) Continuation of application No. 07/859,689, filed as application No. PCT/US90/07289 on Dec. 18, 1990, now abandoned, which is a continuation-in-part of application No. 07/453,570, filed on Dec. 20, 1989, now abandoned.

(51) Int. Cl.$^7$ .............................................. A61K 39/00
(52) U.S. Cl. ...................... 424/184.1; 435/331; 435/335
(58) Field of Search .............................. 530/351, 388.1, 530/388.23, 389.1, 389.2; 424/184.1; 435/331, 335

(56) References Cited

U.S. PATENT DOCUMENTS 5,013,824 A * 5/1991 Abrams et al. ............. 530/300

FOREIGN PATENT DOCUMENTS

| EP | 0230107 | 7/1987 |
| EP | 0254399 | 1/1988 |

OTHER PUBLICATIONS

Goding, Monoclonal Antibodies: Principles & Practice, 1986, pp 198–199.*
Waldman, 1991, Science, 252: 1657–1662, Monoclonal . . . Therapy.*
Ohara et al, 1987, J. Immunol., 139:1127–1134, High . . . Interleukin–4.*
Mossmann et al, 1986, PNAS, 83:5654–5658, T–Cell . . . factor 1.*
Ohara et al, 1985, Nature, 315: 333–336, Production . . . Factor–1.*
Harlow et al, 1988, Antibodies; A Laboratory Manual, pp. 285 & 287.*
Osband et al., Immunol Today, 1990, 11:193.*
Harris et al., TIBTECH, 1993, 11:42.*
Chretien et al., J. Immunol. Meth. 117:67 (1989).
Finkelman et al. Proc. Natl. Acad. Sci. USA 83:9675.
Kohler et al., Nature 256:495 (1975).
Niman et al., Proc. Natl. Acad. Sci. 80.4949 (1983).
Novotny et al., Proc. Natl. Acad. Sci: 83.226 .(1980).
Palfrey man et al., J. Immunol. Meth. 75:383 (1984).
Lerner, Proc. of XVIII Solvay Conf. on Chemistry, Brussels, pp. 43–49 (Nov., Dec. 1983).
Regen Mortel, TIBS (1987).
Ohara et al., Nature 315:333 (1985).
Mossmann et al. Proc. Natl. Acad. Sci. USA 83:5654 (1986).
Ohara et al., J. Immunol:139–1127 (1987).
Deibel et al., Lymphokine Res. 7:(4) 469 (1988).
Butler et al. J. Immunol. 133:25 (1984).
Regenmortel, TIBS 11:36 (1986).
Hopp, J. Immunol. Meth. 88:1 (1986).

* cited by examiner

Primary Examiner—Patrick J. Nolan
(74) Attorney, Agent, or Firm—Immac J. Thampoe; Sandy Gripp

(57) ABSTRACT

Two kinds of antibody antagonists of the binding of human IL-4 to cellular receptors are provided by this invention. Some of the antagonists bind to specific regions of IL-4 which are believed to be involved in interactions between IL-4 and its receptors. Because of this specific binding by the antibodies to the IL-4, the binding of the IL-4 to the receptors is substantially inhibited. The other antibody antagonists of the invention are anti-idiotypic antibodies which, while lacking IL-4 activity, appear to mimic IL-4 and to compete directly with it for binding to the cellular receptors. Polypeptides used to make the antibody antagonists are also provided, together with methods for using the antagonists to inhibit the binding of IL-4 to its cellular receptors.

3 Claims, 7 Drawing Sheets

His-Lys-Cys-Asp-Ile-Thr-Leu-Gln-Glu-Ile-
Ile-Lys-Thr-Leu-Asn-Ser-Leu-Thr-Glu-Gln-
Lys-Thr-Leu-Cys-Thr-Glu-Leu-Thr-Val-Thr-
Asp-Ile-Phe-Ala-Ala-Ser-Lys-Asn-Thr-Thr-
Glu-Lys-Glu-Thr-Phe-Cys-Arg-Ala-Ala-Thr-
Val-Leu-Arg-Gln-Phe-Tyr-Ser-His-His-Glu-
Lys-Asp-Thr-Arg-Cys-Leu-Gly-Ala-Thr-Ala-
Gln-Gln-Phe-His-Arg-His-Lys-Gln-Leu-Ile-
Arg-Phe-Leu-Lys-Arg-Leu-Asp-Arg-Asn-Leu-
Trp-Gyl-Leu-Ala-Gly-Leu-Asn-Ser-Cys-Pro-
Val-Lys-Glu-Ala-Asn-Gln-Ser-Thr-Leu-Glu-
Asn-Phe-Leu-Glu-Arg-Leu-Lys-Thr-Ile-Met-
Arg-Glu-Lys-Tyr-Ser-Lys-Cys-Ser-Ser

FIG. 1

SEQUENCE LISTING

<160> NUMBER OF SEQ ID NOS: 46

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 1

His Lys Cys Asp Ile Thr Leu Gln Glu Ile Ile Lys Thr Leu Asn Ser
 1               5                  10                  15

Leu Thr Glu Gln Lys Thr Leu Cys Thr Glu
            20                  25

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 2

Cys Asp Ile Thr Leu Gln Glu Ile Ile Lys Thr Leu Asn Ser Leu Thr
 1               5                  10                  15

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 3

Thr Glu Gln Lys Thr Leu Cys Thr Glu Leu Thr Val Thr Asp
 1               5                  10

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 4

Asp Ile Phe Ala Ala Ser Lys Asn Thr Thr Glu Lys Glu Thr Phe Cys
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 5

Glu Thr Phe Ser Arg Ala Ala Thr Val Leu Arg Gln Phe Tyr Ser
 1               5                  10                  15

<210> SEQ ID NO 6

```
<211> LENGTH: 14
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 6

Leu Arg Gln Phe Tyr Ser His His Glu Lys Asp Thr Arg Cys
 1               5                  10

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 7

Lys Asp Thr Arg Cys Leu Gly Ala Thr Ala Gln Gln Phe His Arg His
 1               5                  10                  15

Lys Gln Leu Ile Arg Phe
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 8

Leu Lys Arg Leu Asp Arg Asn Leu Trp Gly Leu Ala Gly Leu Asn Ser
 1               5                  10                  15

Cys Pro Val Lys
            20

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 9

Ala Gln Gln Phe His Arg His Lys Gln Leu Ile Arg Phe Leu Lys Arg
 1               5                  10                  15

Leu Asp Arg Asn Leu Trp Gly
            20

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 10

Cys Pro Val Lys Glu Ala Asn Gln Ser Thr Leu Glu Asn
 1               5                  10

<210> SEQ ID NO 11
```

```
<211> LENGTH: 26
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 11

Ala Asn Gln Ser Thr Leu Glu Asn Phe Leu Glu Arg Leu Lys Thr Ile
 1               5                  10                  15

Met Arg Glu Lys Tyr Ser Lys Cys Ser Ser
            20                  25

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 12

Phe Leu Glu Arg Leu Lys Thr Ile Met Arg Glu Lys Tyr Ser Lys Cys
 1               5                  10                  15

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 13

Lys Asp Thr Arg Cys Leu Gly Ala
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 14

Asp Thr Arg Cys Leu Gly Ala Thr
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 15

Thr Arg Cys Leu Gly Ala Thr Ala
 1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide
```

```
<400> SEQUENCE: 16

Arg Cys Leu Gly Ala Thr Ala Gln
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 17

Cys Leu Gly Ala Thr Ala Gln Gln
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 18

Leu Gly Ala Thr Ala Gln Gln Phe
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 19

Gly Ala Thr Ala Gln Gln Phe His
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 20

Ala Thr Ala Gln Gln Phe His Arg
 1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 21

Thr Ala Gln Gln Phe His Arg His
 1               5

<210> SEQ ID NO 22
<211> LENGTH: 8
```

```
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 22

Ala Gln Gln Phe His Arg His Lys
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 23

Gln Gln Phe His Arg His Lys Gln
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 24

Gln Phe His Arg His Lys Gln Leu
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 25

Phe His Arg His Lys Gln Leu Ile
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 26

His Arg His Lys Gln Leu Ile Arg
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 27

Arg His Lys Gln Leu Ile Arg Phe
```

```
<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 28

Arg Ala Ala Thr Val Leu Arg Gln
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 29

Ala Ala Thr Val Leu Arg Gln Phe
  1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 30

Ala Thr Val Leu Arg Gln Phe Tyr
  1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 31

Thr Val Leu Arg Gln Phe Tyr Ser
  1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 32

Val Leu Arg Gln Phe Tyr Ser His
  1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: synthetic
``` polypeptide

<400> SEQUENCE: 33

Leu Arg Gln Phe Tyr Ser His His
  1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 34

Arg Gln Phe Tyr Ser His His Glu
  1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 35

Gln Phe Tyr Ser His His Glu Lys
  1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 36

Phe Tyr Ser His His Glu Lys Asp
  1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 37

Tyr Ser His His Glu Lys Asp Thr
  1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 38

Ser His His Glu Lys Asp Thr Arg
  1               5

<210> SEQ ID NO 39

```
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 39

His His Glu Lys Asp Thr Arg Cys
  1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 40

His Glu Lys Asp Thr Arg Cys Leu
  1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 41

Glu Lys Asp Thr Arg Cys Leu Gly
  1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 42

Lys Asp Thr Arg Cys Leu Gly Ala
  1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 43

Asp Thr Arg Cys Leu Gly Ala Thr
  1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 44
```

```
Thr Arg Cys Leu Gly Ala Thr Ala
  1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 45

Lys Asp Thr Arg Cys
  1               5

<210> SEQ ID NO 46
<211> LENGTH: 129
<212> TYPE: PRT
<213> ORGANISM: Homo sapiens

<400> SEQUENCE: 46

His Lys Cys Asp Ile Thr Leu Gln Glu Ile Ile Lys Thr Leu Asn Ser
  1               5                  10                  15

Leu Thr Glu Gln Lys Thr Leu Cys Thr Glu Leu Thr Val Thr Asp Ile
             20                  25                  30

Phe Ala Ala Ser Lys Asn Thr Thr Glu Lys Glu Thr Phe Cys Arg Ala
         35                  40                  45

Ala Thr Val Leu Arg Gln Phe Tyr Ser His His Glu Lys Asp Thr Arg
     50                  55                  60

Cys Leu Gly Ala Thr Ala Gln Gln Phe His Arg His Lys Gln Leu Ile
 65                  70                  75                  80

Arg Phe Leu Lys Arg Leu Asp Arg Asn Leu Trp Gly Leu Ala Gly Leu
                 85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser
```

ANTIBODY ANTAGONISTS OF HUMAN INTERLEUKIN-4

The present application is a continuation of U.S. application Ser. No. 07/859,689 now abandoned filed on Jun. 11, 1992 which is the United States national application corresponding to International Application No. PCT/US90/07289, filed Dec. 18, 1990 and designating the United States, which PCT application is in turn a continuation-in-part of U.S. application Ser. No. 07/453,570, now abandoned, filed Dec. 20, 1989, the benefit of which applications is claimed pursuant to provisions of 35 U.S.C. §§120, 363, and 365 (C).

BACKGROUND OF THE INVENTION

Interleukin-4 (IL-4) is a protein which affects a broad spectrum of hematopoietic cells [Strober et al., Pediatr. Res. 24:549 (1988)]. IL-4 enhances a number of activities including macrophage function, IgG and IgE production, and the proliferation of immunoglobulin-stimulated B cells, antigen-stimulated T cells and erythropoietin-stimulated red blood cell progenitors. It also increases the proliferation of IL-3-stimulated mast cells.

Together with IgE, mast cells play a central role in allergic reactions. Mast cells are granule-containing connective tissue cells which are located proximally to capillaries throughout the body, with especially high concentrations in the lungs, skin and gastrointestinal and genitourinary tracts. Following exposure to an antigenic substance, mast cells degranulate and release chemical mediators such as histamine, serotonin, heparin, prostaglandins etc. to produce an allergic reaction.

Because of the stimulatory effects of IL-4 on IgE production and mast cell proliferation, an antagonist of IL-4 may be useful for the treatment of allergies by decreasing mast cell growth and IgE production.

Some investigators have used antibodies to antagonize the biological activity of IL-4. For example, Finkelman et al. [Proc. Natl. Acad. Sci. USA 83:9675 (1986)] used a monoclonal antibody against BSF-1 (now called IL-4) to inhibit IL-4-induced production of IgE in mice infected with the nematode parasite *Nippostrongylus brasiliensis* or injected with a purified goat antibody to mouse IgD. Both treatments were known to stimulate IgE production; the latter treatment was also known to stimulate IL-4 secretion.

More recently, Chretien et al. [J. Immunol. Meth. 117:67 (1989)] reported that polyclonal rabbit antiserum to partially purified recombinant human IL-4 neutralized some of the biological activities of IL-4 in vitro. Monoclonal antibodies against synthetic polypeptides having amino acid sequences corresponding to residues 3–18, 31–46, 52–65 and 112–127 of mature human IL-4, however, failed to neutralize the bioactivity of IL-4 although they bound to the protein.

SUMMARY OF THE INVENTION

This invention provides polypeptides containing from about 5 to about 26 amino acid residues which have amino acid sequences corresponding to the sequence of amino acid residues 61 to 82 or 104 to 129 of human IL-4, or a subsequence thereof. Preferred polypeptides have the amino acid sequences Lys-Asp-Thr-Arg-Cys (SEQ.ID.NO.: 45),
Thr-Ala-Gln-Gln-Phe-His-Arg-His (SEQ.ID.NO.: 21),
Lys-Asp-Thr-Arg-Cys-Leu-Gly-Ala-Thr-Ala-Gln-Gln-Phe-His-Arg-His-Lys-Gln-Leu-Ile-Arg-Phe (SEQ.ID.NO.: 7), and
Ala-Asn-Gln-Ser-Thr-Leu-Glu-Asn-Phe-Leu-Glu-Arg-Leu-Lys-Thr-Ile-Met-Arg-Glu-Lys-Tyr-Ser-Lys-Cys-Ser-Ser (SEQ.ID.NO.: 11).

The present invention further provides antibodies which inhibit the binding of human IL-4 to cellular receptors and specifically bind to such IL-4 and to polypeptides containing from about 5 to about 26 amino acid residues and having amino acid sequences corresponding to the sequence of amino acid residues 61 to 82 or 104 to 129 of human IL-4, or a subsequence thereof, which antibodies inhibit the binding of human IL-4 to cellular receptors.

This invention still further provides methods for making antibodies which specifically bind to and inhibit the binding of human IL-4 to cellular receptors, comprising administering to an animal a sufficient quantity of a polypeptide containing from about 5 to about 26 amino acid residues and having an amino acid sequence corresponding to the sequence of amino acid residues 61 to 82 or 104 to 129 of human IL-4, or a subsequence thereof, whereby the animal produces antibodies against the polypeptide which specifically bind to human IL-4 and inhibit the binding of human IL-4 to cellular receptors.

This invention still further provides anti-idiotypic antibodies against the above-mentioned antibodies. These antibodies presumably antagonize the biological activity of IL-4 by competing with IL-4 for binding to its cellular receptors.

This invention still further provides a method for inhibiting the binding of human IL-4 to cellular receptors, comprising contacting human IL-4 with an antibody which specifically binds to human IL-4 and to a polypeptide containing from about 5 to about 26 amino acid residues and having an amino acid sequence corresponding to the sequence of amino acid residues 61 to 82 or 104 to 129 of human IL-4, or a subsequence thereof, which antibody inhibits the binding of human IL-4 to cellular receptors.

This invention still further provides a method for inhibiting the binding of human IL-4 to cellular receptors, comprising contacting cells bearing receptors for human IL-4 with anti-idiotypic antibodies against an antibody which specifically binds to human IL-4 and to a polypeptide containing from about 5 to about 26 amino acid residues and having an amino acid sequence corresponding to the sequence of amino acid residues 61 to 82 or 104 to 129 of human IL-4, or a subsequence thereof, which anti-idiotypic antibodies inhibit the binding of human IL-4 to cellular receptors.

The antibody antagonists of the invention are useful in in vitro receptor binding studies to determine the mechanism of action of IL-4 and/or to identify agonists or other antagonists of IL-4. As noted above, they may also be useful for the treatment of allergies by decreasing IL-4-stimulated mast cell proliferation and IgE production.

BRIEF DESCRIPTION OF THE FIGURES

This invention can be more readily understood by reference to the accompanying figures, in which:

FIG. 1 shows the amino acid sequence of mature human IL4, from the amino- to the carboxyl-terminus.

DESCRIPTION OF THE INVENTION

Figure 2:
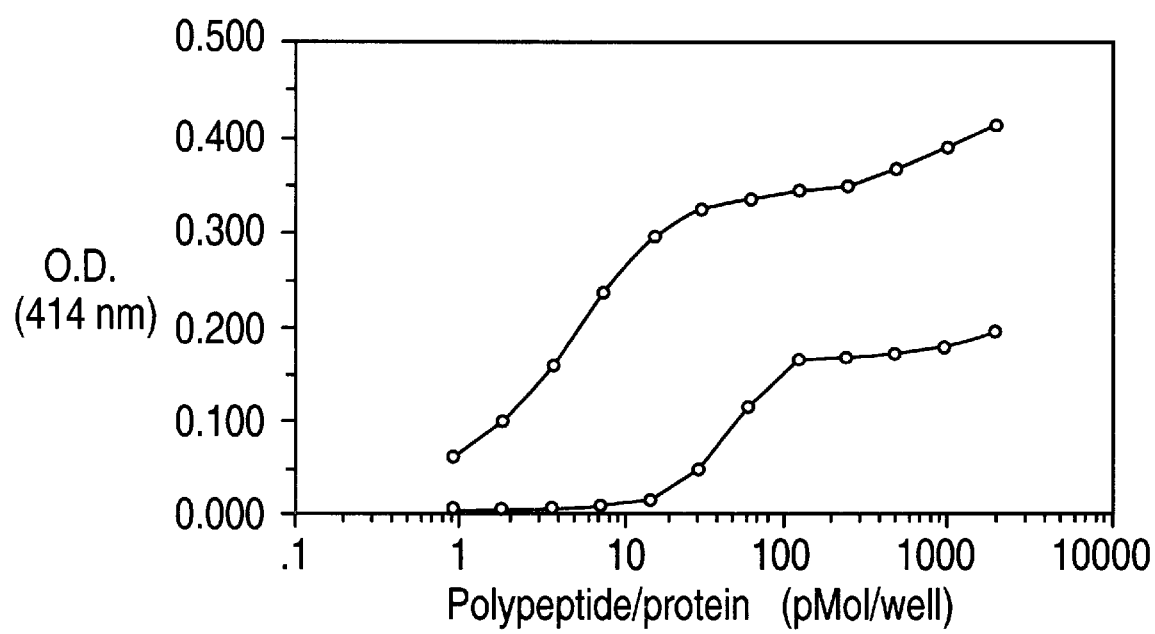
FIG. 2 is a graphical representation of the binding of IL-4 (lower curve) and polypeptide No. 7 (upper curve; see Table 1) by a rabbit IgG fraction against the polypeptide, in direct ELISA analyses. The amount of protein/polypeptide bound in picomoles is shown as a function of absorbance at 414 nm.

All references cited herein are hereby incorporated in their entirely by reference. Amino acid sequences of polypeptides shown are in the standard one-letter or three-letter form (Lehninger, Principles of Biochemistry, 1982, Worth Publishers Inc., New York, p. 96).

The present invention provides antibodies which antagonize the binding of human IL-4 to cellular receptors by (a) combining with a region of the IL-4 which apparently is involved in interactions with the receptors or by (b) mimicking IL-4 itself, thereby competing with it for binding to the cellular receptors. Because IL-4 stimulates the production of IgE antibodies and the proliferation of mast cells, two effectors of allergic responses, the antibody antagonists of the invention are useful in the treatment of allergies. They also are useful in vitro IL-4 receptor binding systems, to elucidate the mechanism of action of IL-4 or to screen for other IL-4 antagonists or agonists.

As used herein, human "IL-4" means a protein which (a) has an amino acid sequence that is substantially identical to the sequence of mature, human IL-4 shown in FIG. 1 and (b) has biological activity that is common to native IL-4.

Substantial identity of amino acid sequences means that the sequence of another IL-4 compared to the sequence of FIG. 1 is identical or differs by one or more amino acid alterations (deletions, additions, substitutions) that do not substantially impair biological activity.

Of course, the amino acid sequences in the IL-4 regions mentioned above may differ in the case of substantially identical IL-4s.

Investigations with synthetic polypeptides described below have shown that there are two regions within the human IL-4 molecule which appear to be involved in receptor binding. For convenient reference, the amino acid sequences of these polypeptides will be defined herein by the positions of the residues in the amino acid sequence of mature human IL-4 shown in FIG. 1, with 1 being the amino-terminal histidine residue and 129 being the carboxyl-terminal serine residue.

As a result of these investigations, it has been found that synthetic polypeptides having amino acid sequences corresponding to the sequences of residues 52 to 82 and 104 to 129 or subsequences thereof of human IL-4 can be used as antigens to elicit the production in animals of antibodies which can bind to the polypeptides and to human IL-4. Because of their ability to bind to such specific regions of IL-4, the. antibodies of the invention inhibit at least 60% of the specific binding of $^{125}$I-IL-4 to cells bearing receptors for IL-4.

The largest of the foregoing binding regions of IL-4 (residues 52–82) contains about 30 amino acid residues. It is well known in the art that antigenic determinants (epitopes) generally contain at least about 5 amino acid residues [Ohno et al., Proc. Natl. Acad. Sci. USA 82:2945 (1985)]. Therefore, the polypeptides of the invention comprise from about 5 to about 30 amino acid residues and have the above-mentioned amino acid sequences. Whether a given polypeptide falls within the scope of this invention can readily be determined by routine experimentation using the methods described below.

The polypeptides are synthesized by a suitable method such as by exclusive solid phase synthesis, partial solid phase methods, fragment condensation or classical solution synthesis. The polypeptides are preferably prepared by solid phase peptide synthesis as described by Merrifield, J. Am. Chem. Soc. 85:2149 (1963). The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aromatic urethane type protecting groups [e.g., benzyloxycarbonyl (Cbz), substituted benzyloxycarbonyl and 9-fluorenylmethyloxycarbonyl (Fmoc)], aliphatic urethane protecting groups [e.g., t-butyloxycarbonyl (Boc), isopropyloxycarbonyl, cyclohexyloxycarbonyl] and alkyl type protecting groups (e.g., benzyl, triphenylmethyl). The preferred protecting group is Boc. The side-chain protecting groups for Tyr include tetrahydropyranyl, tert-butyl, trityl, benzyl, Cbz, 4-Br-Cbz and 2,6-dichlorobenzyl. The preferred side-chain protecting group for Tyr is 2,6-dichlorobenzyl. The side-chain protecting groups for Asp include benzyl, 2,6-dichlorobenzyl, methyl, ethyl and cyclohexyl. The preferred side-chain protecting group for Asp is cyclohexyl. The side-chain protecting groups for Thr and Ser include acetyl, benzoyl, trityl, tetrahydropyranyl, benzyl, 2,6-dichlorobenzyl and Cbz. The preferred protecting group for Thr and Ser is benzyl. The side-chain protecting groups for Arg include nitro, Tos, Cbz, adamantyloxycarbonyl and Boc. The preferred protecting group for Arg is Tos. The side-chain amino group of Lys may be protected with Cbz, 2-Cl-Cbz, Tos or Boc. The 2-Cl-Cbz group is the preferred protecting group for Lys.

The side-chain protecting groups selected must remain intact during coupling and not be removed during the deprotection of the amino-terminus protecting group or during coupling conditions.

The side-chain protecting groups must also be removable upon the completion of synthesis, using reaction conditions that will not alter the finished polypeptide.

Solid phase synthesis is usually carried out from the carboxyl-terminus by coupling the alpha-amino protected (side-chain protected) amino acid to a suitable solid support. An ester linkage is formed when the attachment is made to a chloromethyl or hydroxymethyl resin, and the resulting polypeptide will have a free carboxyl group at the C-terminus. Alternatively, when a benzhydrylamine or p-methylbenzhydrylamine resin is used, an amide bond is formed and the resulting polypeptide will have a carboxamide group at the C-terminus. These resins are commercially available, and their preparation has described by Stewart et al., "Solid Phase Peptide Synthesis" (2nd Edition), Pierce Chemical Co., Rockford, Ill., 1984.

The C-terminal amino acid, protected at the side-chain if necessary and at the alpha-amino group, is coupled to the benzhydrylamine resin using various activating agents including dicyclohexylcarbodiimide (DCC), N,N'-diisopropylcarbodiimide and carbonyldiimidazole. Following the attachment to the resin support, the alpha-amino protecting group is removed using trifluoroacetic acid (TFA) or HCl in dioxane at a temperature between 0° and 25° C. Dimethylsulfide is added to the TFA after the introduction of methionine (Met) to suppress possible S-alkylation. After removal of the alpha-amino protecting group, the remaining protected amino acids are coupled stepwise in the required order to obtain the desired sequence.

Various activating agents can be used for the coupling reactions including DCC, N,N'-diisopropylcarbodiimide, benzotriazol-1-yl-oxy-tris-(dimethylamino)-phosphonium hexafluorophosphate (BOP) and DCC-hydroxybenzotriazole (HOBt). Each protected amino acid is used in excess (>2.0 equivalents), and the couplings are usually carried out in N-methylpyrrolidone (NMP) or in DMF, $CH_2Cl_2$ or mixtures thereof. The extent of completion of the coupling reaction is monitored at each stage, e.g., by the ninhydrin reaction as described by Kaiser et al., Anal. Biochem. 34:595 (1970). In cases where incomplete coupling is found, the coupling reaction is repeated. The coupling reactions can be performed automatically with commercially available instruments.

After the entire assembly of the desired polypeptide, the polypeptide-resin is cleaved with a reagent such as liquid HF for 1–2 hours at 0° C., which cleaves the polypeptide from the resin and removes all side-chain protecting groups. A scavenger such as anisole is usually used with the liquid HF to prevent cations formed during the cleavage from alkylating the amino acid residues present in the polypeptide. The polypeptide-resin may be deprotected with TFA/dithioethane prior to cleavage if desired.

Side-chain to side-chain cyclization on the solid support requires the use of an orthogonal protection scheme which enables selective cleavage of the side-chain functions of acidic amino acids (e.g., Asp) and the basic amino acids (e.g., Lys). The 9-fluorenylmethyl (Fm) protecting group for the side-chain of Asp and the 9-fluorenylmethyloxycarbonyl (Fmoc) protecting group for the side-chain of Lys can be used for this purpose. In these cases, the side-chain protecting groups of the Boc-protected polypeptide-resin are selectively removed with piperidine in DMF. Cyclization is achieved on the solid support using various activating agents including DCC, DCC/HOBt or BOP. The HF reaction is carried out on the cyclized polypeptide-resin as described above.

Recombinant DNA methodology can also be used to prepare the polypeptides. The known genetic code, tailored if desired with known preferred codons for more efficient expression in a given host organism, can be used to synthesize oligonucleotides encoding the desired amino acid sequences. The phosphoramidite solid support method of Matteucci et al., [J. Am. Chem. Soc. 10:3185 (1981)] or other known methods can be used for such syntheses. The resulting oligonucleotides can be inserted into an appropriate vector and expressed in a compatible host organism.

The polypeptides of the invention can be purified using HPLC, gel filtration, ion exchange and partition chromatography, countercurrent distribution or other well known methods.

Antibodies can be prepared against the polypeptides of the invention using standard methods. As used herein, the word "antibody" refers to both polyclonal and monoclonal antibodies. It also includes whole immunoglobulins and antigen binding fragments thereof.

The polyclonal antibodies can be produced by immunizing a host animal such as a rabbit, rat, goat, sheep, mouse, etc. with one of the polypeptides. Preferably, one or more booster injections are given after the initial injection, to increase the antibody titer. Blood is then drawn from the animal and serum is prepared and screened by standard methods such as enzyme-linked immunosorbent assay (ELISA) using the polypeptide as the antigen.

Preferably, the immunogenicity of the polypeptides is increased by combination with an adjuvant and/or by conversion to a larger form prior to immunization.

Suitable adjuvants for the vaccination of animals include but are not limited to Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecylammonium bromide, N,N-dioctadecyl-N',N'-bis(2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The polypeptides could also be administered following incorporation into liposomes or other microcarriers.

The immunogenicity of the polypeptides can also be enhanced by cross-linking or by coupling to an immunogenic carrier molecule (i.e., a macromolecule having the property of independently eliciting an immunological response in a host animal, to which the polypeptides of the invention can be covalently linked). Cross-linking or conjugation to a carrier molecule may be required because small polypeptides sometimes act as haptens (molecules which are capable of specifically binding to an antibody but incapable of eliciting antibody production, i.e., they are not immunogenic). Conjugation of such polypeptides to an immunogenic carrier molecule renders the fragments immunogenic through what is commonly known as the "carrier effect".

Suitable carrier molecules include, e.g., proteins and natural or synthetic polymeric compounds such as polypeptides, polysaccharides, lipopolysaccharides etc. A useful carrier is a glycoside called Quil A. which has been described by Morein et al., Nature 308:457 (1984). Protein carrier molecules are especially preferred, including but not limited to keyhole limpet hemocyanin and mammalian serum proteins such as human or bovine gammaglobulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the polypeptides are to be elicited.

Covalent coupling to the carrier molecule can be carried out using methods well known in the art, the exact choice of which will be dictated by the nature of the carrier molecule used. When the immunogenic carrier molecule is a protein, the polypeptides of the invention can be coupled, e.g., using water soluble carbodiimides such as dicyclohexylcarbodiimide or glutaraldehyde.

Coupling agents such as these can also be used to cross-link the polypeptides to themselves without the use of a separate carrier molecule. Such cross-linking into aggregates can also increase immunogenicity.

Serum produced from animals thus immunized can be used directly. Alternatively, the IgG fraction can be separated from the serum using standard methods such as plasmaphoresis or adsorption chromatography using IgG specific adsorbents such as immobilized Protein A.

Monoclonal antibodies can be prepared using standard methods, e.g., as described by Kohler et al., [Nature 256:495 (1975); Eur. J. Immunol. 6:511 (1976)]. Essentially, an animal is immunized as described above to produce antibody-secreting somatic cells. These cells are then removed from the immunized animal for fusion to myeloma cells.

Somatic cells with the potential to produce antibodies, particularly B cells, are suitable for fusion with a myeloma cell line. These somatic cells may be derived from the lymph nodes, spleens and peripheral blood of primed animals. In the exemplary embodiment of this invention mouse spleen cells are used, in part because these cells produce a relatively high percentage of stable fusions with mouse myeloma lines. It would be possible, however, to use rat, rabbit, frog or other cells instead.

Specialized myeloma cell lines have been developed from lymphocytic tumors for use in hyridoma-producing fusion procedures [Kohler and Milstein, Eur. J. Immunol. 6:511 (1976); Shulman et al., Nature 276:269 (1978); Volk et al., J. Virol. 42:220 (1982)]. These cell lines have been developed for at least three reasons. The first is to facilitate the selection of fused hybridomas from unfused and similarly indefinitely self-propagating myeloma cells. Usually, this is accomplished by using myelomas with enzyme deficiencies that render them incapable of growing in certain selective media that support the growth of hybridomas. The second reason arises from the inherent ability of lymphocytic tumor cells to produce their own antibodies. The purpose of using monoclonal techniques is to obtain fused hybrid cell lines with unlimited lifespans that produce the desired single antibody under the genetic control of the somatic cell component of the hybridoma. To eliminate the production of tumor cell antibodies by the, hybridomas, myeloma cell lines incapable of producing light or heavy immunoglobulin chains or deficient in antibody secretion mechanisms are used. A third reason for selection of these cell lines is for their suitability and efficiency for fusion.

Many myeloma cell lines may be used for the production of fused cell hybrids, including, e.g., P3X63-Ag8, P3/NS1-Ag4–1 (NS-1), Sp2/0-Ag14 and S194/5.XXO.Bu.1. The P3X63-Ag8 and NS-1 cell lines have been described by Kohler and Milstein [Eur. J. Immunol. 6:511 (1976)]. Shulman et al. [Nature 276:269 (1978)] developed the Sp2/0-Ag14 myeloma line. The S194/5.XXO.Bu.1 line was reported by Trowbridge [J. Exp. Med. 148:313 (1979)].

Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described by Kohler and Milstein, supra, Gefter et al., [Somatic Cell Genet. 3:231 (1977)], and Volk et al., (J. Virol. 42:220 (1982)]. The fusion-promoting agents used by those investigators were Sendai virus and polyethylene glycol (PEG). The fusion procedure of the example of the present invention uses PEG.

Because fusion procedures produce viable hybrids at very low frequency e.g., when spleens are used as a source of somatic cells, only one hybrid is obtained for roughly every $1 \times 10^5$ spleen cells), it is essential to have a means of selecting the fused cell hybrids from the remaining unfused cells, particularly the unfused myeloma cells. A means of detecting the desired antibody-producing hybridomas among other resulting fused cell hybrids is also necessary.

Generally, the selection of fused cell hybrids is accomplished by culturing the cells in media that support the growth of hybridomas but prevent the growth of the unfused myeloma cells, which normally would go on dividing indefinitely. The somatic cells used in the fusion do not maintain long-term viability in in vitro culture and hence do not pose a problem. In the example of the present invention, myeloma cells lacking hypoxanthine phosphoribosyl transferase (HPRT-negative) were used. Selection against these cells is made in hypoxanthine/aminopterin/thymidine (HAT) medium, a medium in which the fused cell hybrids survive due to the HPRT-positive genotype of the spleen cells. The use of myeloma cells with different genetic deficiencies (drug sensitivities, etc.) that can be selected against in media supporting the growth of genotypically competent hybrids is also possible.

Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radio-immunoassay techniques which have been described in the literature [see, e.g., Kennet et al. (editors), Monoclonal Antibodies and Hybridomas: A New Dimension in Biological Analyses, pp. 376–384, Plenum Press, New York (1980)].

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumors that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation.

Whether anti-polypeptide antibodies made as described above are suitable for use in this invention is determined by a two-part screening procedure involving (a) ELISA analysis using the immunizing polypeptide and human IL-4 as antigens and (b) radioligand receptor binding analysis, in which inhibition of the specific binding of $^{125}$I-IL-4 to cellular receptors is measured.

Recombinant human IL-4 for use in such assays is an article of commerce, available, e.g., from Genzyme Corporation, Boston, Mass. Alternatively, it can be produced using the known nucleotide sequence of the IL-4 gene [Yokoto et al., Proc. Natl[. Acad. Sci. USA 83:5894 (1986)] and standard recombinant DNA methods [see, e.g., International Patent Application Publication No. WO 87/02990; Kimmenade et al., Eur. J. Biochem. 173:109 (1988)].

ELISA analysis is carried out by standard methods such as the method of Chretien et al., [J. Immunol. Meth. 117:67 (1989)], using a polypeptide or IL-4 adsorbed to a microtiter plate. The presence of antibodies bound to the immobilized polypeptide or protein is detected with a labeled anti-IgG second antibody. Such second antibodies are preferably labeled with an enzyme such as a peroxidase, glucose oxidase, b-galactosidase or alkaline phosphatase. Horseradish peroxidase can be detected by spectrophotometric analysis of its activity on a substrate such as pyrogallol, o-phenylenediamine or 2,2'-azino-bis(3-ethyl-benzthiazoline-6-sulfonic acid).

Antibodies found to specifically bind to both the immunizing polypeptide and IL-4 are further evaluated for the ability to inhibit the specific binding of labeled IL-4 to receptors on appropriate target cells. The anti-polypeptide antibodies of the invention are characterized by an ability to inhibit at least 60% of such binding.

Any cells bearing IL-4 receptors such as Jijoye, U-937, CCRF-CEM and CEM-CM3 cells can be used to carry out the binding assay, but Daudi cells are convenient and readily available. Daudi cells are a well-characterized B lymphoblast cell line derived from a Burkitt lymphoma patient which can be purchased from the American Type Culture Collection under Accession No. ATCC CCL 213. $^{125}$I-IL-4 for use in the assay can be prepared by labeling IL-4 with iodine-125 using, e.g., the lactoperoxidase method [David et al., Biochemistry 133:1014 (1974)] or the method of Bolton et al., [Biochem. J. 13:529 (1973)]. Glycosylated recombinant human IL-4 is an article of commerce, available for purchase, e.g., from Genzyme Corporation, Boston, Mass.

The anti-idiotypic antibodies of the invention are directed against antibodies specific for the IL-4 antigenic determinants present in the polypeptides of the invention. Such anti-idiotypic antibodies mimic or act like the original antigenic determinants (see, e.g., U.S. Pat. No. 4,731,237 to Reagan et al.). Like IL-4 itself, these antibodies are presumed to bind specifically and directly to IL-4 receptors. The anti-idiotypic antibodies, however, do not possess the biological activity of IL-4.

Such anti-idiotypic antibodies are prepared by vaccinating an animal with an antibody (polyclonal or monoclonal) against a polypeptide of the invention. They may be recovered as a whole polyclonal antiserum or as an IgG fraction thereof, or as monoclonal antibodies produced by cloned hybridomas, as described above.

Pharmaceutical compositions can be prepared which contain effective amounts of one or more of the antibodies of the invention and a physiologically acceptable carrier. Such carriers are well known to those skilled in the art. The antibodies can be administered directly or in the form of a composition to a human patient for the treatment of allergies or other conditions mediated by IL-4. The pharmaceutical compositions are made by admixing a physiologically acceptable carrier with an effective amount of one or more of the antibodies.

Determination of the proper dosage of an antibody of the invention for a particular situation is within the skill of the art. Generally, treatment is initiated with smaller dosages that are less than optimum. Thereafter, the dosage is increased by small increments until the optimum effect under the circumstances is reached. For convenience, the total daily dosage may be divided and administered in portions during the day if desired.

The amount and frequency of administration of the antibodies of the invention will be regulated according to the judgment of the attending clinician, taking into account such factors as age, condition and size of the patient and severity of the symptom(s) being treated.

EXAMPLES

Unless otherwise specified, percentages given below for solids in solid mixtures, liquids in liquids and solids in liquids are on a wt/wt, vol/vol and wt/vol basis, respectively.

Protein determinations were carried out by the method of Lowry et al., [J. Biol. Chem. 193:265 (1951)] using bovine serum albumin as a standard. Bioassay of IL-4 was performed as described by Mossman [J. Immunol. Methods 65:55 (1983)], measuring stimulation of cell proliferation as MTT (3-[4,5-Dimethylthiazol-2-yl]-2,5-diphenyltetrazolium bromide) uptake in PHA-stimulated human peripheral blood lymphocytes. One unit of IL-4 activity is an amount of IL-4 which causes half-maximal stimulation in $2 \times 10^5$ cells in the assay. One microgram of pure human IL-4 has about 20,000 units of activity in the assay.

Polypeptide Synthesis

A number of polypeptides were synthesized, the amino acid sequences of which, taken together, correspond to the amino acid sequence of the entire mature human IL-4 protein.

The polypeptides were synthesized using the solid-phase method of Merrifield [J. Am. Chem. Soc. 85:2149 (1963)] and an Applied Biosystems Model 430A synthesizer. The t-butyloxycarbonyl amino protecting group and symmetrical anhydrides were employed. Following removal of the protecting groups, the polypeptides were cleaved from the resin with hydrogen fluoride.

Purification of the polypeptides was carried out by reversed-phase HPLC using a Rainin Dynamax® C-8 column developed with a gradient of acetonitrile in 0.1% trifluoroacetic acid. The eluate was monitored by ultraviolet absorbance at 214 nm. The identities of the purified polypeptides were confirmed by amino acid sequencing and mass spectral analysis, using standard methods.

The polypeptides produced, their amino acid sequences and the residues of mature human IL-4 (i.e., without a signal peptide; see FIG. 1) to which the polypeptide sequences correspond are shown in Table 1.

TABLE 1
Structures of the Synthetic Polypeptides

| SEQ. ID. NO. | Polypeptide No. | Sequence | Corresponding IL-4 Residues |
|---|---|---|---|
| 1 | 1 | HKCDITLQEIIKTLNSLTEQKTLCTE | 1–26 |
| 2 | 2 | CDITLQEIIKTLNSLT | 3–18 |
| 3 | 3 | TEQKTLCTELTVTD | 18–31 |
| 4 | 4 | DIFAASKNTTEKETFC | 31–46 |
| 5 | 5 | ETFSRAATVLRQFYS* | 43–57 |
| 6 | 6 | LRQFYSHHEKDTRC | 52–65 |
| 7 | 7 | KDTRCLGATAQQFHRHKQLIRF | 61–82 |
| 8 | 8 | LKRLDRNLWGLAGLNSCPVK | 83–102 |
| 9 | 9 | AQQFHRHKQLIRFLKRLDRNLWG | 70–92 |
| 10 | 10 | CPVKEANQSTLEN | 99–111 |
| 11 | 11 | ANQSTLENFLERLKTIMREKYSKCSS | 104–129 |
| 12 | 12 | FLERLKTIMREKYSKC | 112–127 |

*The amino acid sequence of polypeptide No. 5 corresponds to residues 43–57 of human IL-4, except that the cysteine residue at position 46 of human IL-4 has been replaced by a serine residue in the polypeptide.

Hydrophilicity analysis of human IL-4 carried out by Hopp et al., [Proc. Natl. Acad. Sci. USA 78:3824 (1981)] shows that the region corresponding to polypeptide No. 7 contains both hydrophilic and hydrophobic residues which are predicted by secondary structure models to possibly form an alpha helical region in IL-4.

Preparation and Characterization of Anti-Polypeptide Antibodies

Two milligrams of polypeptide No. 7 (Table 1) corresponding to residues 61–82 of human IL-4 were dissolved in 0.4 ml of 0.5 M Tris-HCl, pH 6.8, and 0.1 ml of pertussis vaccine (source, strain 18334, heat killed, 20 Units/ml, 1/10,000 dilution thimersal). Freund's complete adjuvant (0.5 ml) was added, and the sample was homogenized in a syringe. New Zealand white rabbits were each immunized with 1 ml of the sample by 0.1 ml (200 µg polypeptide) intradermal injections.

After a period of about four months and periodically thereafter, booster injections were given as above. Blood was periodically withdrawn from the ear or femur veins of the rabbits and allowed to clot.

An IgG fraction was isolated from the serum of one of the rabbits by adsorbing the same onto a Protein A-Sepharose® column (Pharmacia, Piscataway, N.J.) equilibrated with 1.5 M glycine buffer, pH 8.9. Chromatography was carried out using standard methods by Forton Biochem. Co. The purified material was judged to be about 98% pure IgG by SDS polyacrylamide gel electrophoresis [Laemmli, Nature 227:680 (1970)]. This material was designated the antiserum 343-6 IgG fraction.

Using similar methods, IgG fractions of antisera against the other polypeptides shown in Table 1 were also prepared.

ELISA was carried out on the isolated IgG fractions by coating 96-well microtiter plates (Becton-Dickinson) with about 0.25 µg of one of the various polypeptides in 50 µl of Tris-buffered saline (TBS; 50 mM Tris, 0.15 M NaCl, pH 7.0) for one hour at room temperature. Following this incubation, the wells were washed five times with TBS containing 0.1% Tween 20 (polyoxyethylenesorbitan monolaurate).

The washed wells were blocked with 1% bovine serum albumin (BSA) in TBS for 1 hour at room temperature, washed five times with TBS, blocked with 0.1% nonspecific IgG in TBS for 2 hours at room temperature, and washed five times as described above. Fifty-microliter aliquots of various dilutions of the IgG fractions in TBS were then added to the wells, and the plates were incubated at room temperature for 1 hour and then washed in the same way as before.

To each well was added 50 µl of TBS containing 2.5 ng of horseradish peroxidase-labeled goat anti-rabbit IgG, and the plates were incubated for 1 hour at room temperature. After washing as above, the wells were developed with hydrogen peroxide and 2,2-Azino-di-(3-ethyl-benzthiazoline sulfonate).

Control wells were also developed in which one of the three assay components (i.e., antigen, antibody or labeled second antibody) was deleted. Samples were read in a Dynatech Model 650 spectrophotometer.

The results of such analysis carried out on the antiserum 343-6 IgG fraction using polypeptide No. 7 (Table 1) and human IL-4 as antigens are shown in FIG. 2. There, where absorbance at 414 nm as a measure of antigen binding is shown as a function of the amount of polypeptide or IL-4 per well, it can be seen that the antibodies bound to both antigens. To produce these results, the antiserum 343-6 IgG fraction was diluted 1:200 prior to coating 50 µl aliquots onto the wells.

To determine whether antibodies in the anti-polypeptide IgG fractions, by specifically binding to human IL-4, could thereby inhibit the binding of the IL-4 to cellular receptors, radioligand binding analyses were carried out.

Purified recombinant human IL-4 expressed in CHO cells [Le et al., J. Biol. Chem. 263:10817 (1988)] was labeled with iodine-125 by a modification of the method of Bolton et al., [Biochem. J. 133:529 (1973)], using Bolton-Hunter reagent from DuPont-NEN, Boston, Mass. Briefly, 2 mCi of the Bolton-Hunter reagent were reacted with 5.0 µg of the purified IL-4 in 100 µl of 50 mM sodium phosphate buffer, pH 8.0, for 2 hours at 22° C. The reaction was quenched for 1 hour by the addition of an equal volume of 1.0 M glycine.

The iodinated protein was isolated by gel filtration in a PD-1 column (Pharmacia, Piscataway, N.J.) equilibrated with 0.2% gelatin in 50 mM sodium phosphate, pH 7.4. Radioactive material eluting from the column in the void volume was pooled and analyzed. The specific radioactivity of the labeled IL-4 was 1500 Ci/mmole as determined by the self displacement method of Calvo et al., Biochem. J. 212:259 (1983)], and the molar incorporation ratio was 0.68 mole of iodine per mole of protein.

One-tenth milliliter volumes of serial dilutions of the various anti-polypeptide IgG fractions in binding medium

[RPMI 1640 with 10% fetal calf serum (FCS)] were incubated with constant amounts of $^{125}$I-IL-4 (about 2×10$^5$ cpm) in 1.0 ml of binding medium in 1.5 ml tubes for 18 hours at 4° C. prior to performance of binding assays. Following this preincubation, the contents of the tubes were combined with 2×10$^6$ Daudi cells, and the mixtures were incubated for 2 hours at 4° C.

Following the incubation, the cells were pelleted by centrifugation at 800 or 12,000×g for 30 seconds at 4° C., and the supernatants were discarded. The cells were resuspended in 0.1 ml of fresh binding medium without labeled IL-4 at 4° C., pelleted as above, resuspended in 100 μl of assay medium and overlaid on 100 μl of dibutyl phthalate and dioctyl phthalate (1:1). The cells were pelleted at 13,000×g for 2 minutes, frozen in liquid nitrogen and were then counted in a gamma counter. Nonspecific binding was determined in parallel samples containing 1.0 mg of unlabeled human IL-4.

The results of the foregoing analyses are shown in Table 2.

TABLE 2

Analysis of Anti-Polypeptide IgG Fractions

| Polypeptide Used As Antigen[a] | Antibody Reactivity With[b] | | % Inhibition of $^{125}$I-IL-4 Binding |
|---|---|---|---|
| | Polypeptide | IL-4 | |
| 1 | + | − | 0 |
| 2 | + | + | 0 |
| 3 | + | + | 2.4 |
| 4 | + | + | 0 |
| 5 | + | + | 8.7 |
| 6 | + | + | 76 |
| 7 | + | + | 78 |
| 8 | + | − | 7.5 |
| 9 | + | + | 39 |
| 10 | + | + | 26 |
| 11 | + | + | 60 |
| 12 | + | + | 0 |

[a]The amino acid sequences of the polypeptides and the corresponding regions within the human IL-4 molecule are shown in Table 1.
[b]In determining antibody reactivity, + means an absorbance at 414 mn > 0.05, after subtracting the absorbance of control wells.

The data of Table 2 show that antibodies produced against polypeptides corresponding to residues 52–65 (polypeptide No. 6), 61–82 (polypeptide No. 7) and 104–129 (polypeptide No. 11) of human IL-4 were strong inhibitors of the binding of the $^{125}$I-IL-4 to the Daudi cells. These antibodies specifically bound to both the immunizing polypeptides and to the IL-4, although pre-immune serum bound to neither and had no effect on receptor binding.

As further shown in Table 2, the antibodies against polypeptides 6 and 7 were equally potent in inhibiting the binding of the labeled IL-4. Table 1 shows that these polypeptides share a common KDTRC amino acid subsequence. Such combined evidence suggests that this subsequence may constitute an important epitope and provides support for polypeptides of the invention which may contain as few as 5 amino acid residues.

The binding inhibition produced by the polyclonal antibodies against polypeptide No. 6 is particularly interesting. As noted above, Chretien et al., found that a monoclonal antibody produced against the same polypeptide did not neutralize the bioactivity of IL-4. Subsequent epitope analysis described below, however, has shown that antibody is probably directed against residues toward the. amino terminus of the polypeptide, not against the Lys-Asp-Thr-Arg-Cys subsequence at the carboxyl-terminus. Presumably, the polyclonal antiserum of this example inhibited IL-4 binding because some of the antibodies in it were directed against the epitope comprising this specific subsequence.

Figure 3:
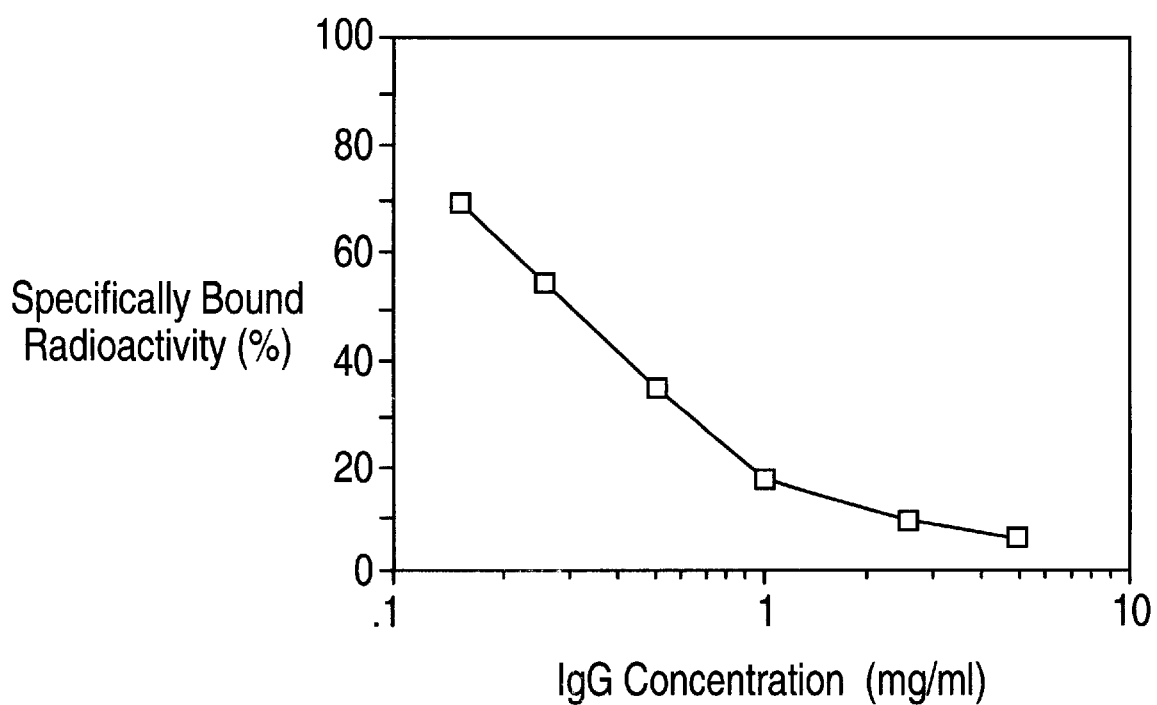
FIG. 3 is a graphical representation of the inhibition of the specific binding of $^{125}$I-IL-4 to Daudi cells by a rabbit IgG fraction against polypeptide No. 7, showing percent specifically bound radioactivity as a function of increasing IgG concentration.

The results obtained with the antiserum 343-6 IgG fraction against polypeptide No. 7 are shown graphically in FIG. 3, wherein 2×10$^6$ Daudi cells were incubated with 50 pM $^{125}$I-IL-4 and the indicated antibody concentrations for 2 hours at 4° C. Specific binding in the absence of antibody was 3,347 cpm. The strong binding inhibition observed, coupled with the fact that the antibodies specifically bound to polypeptide No. 7 and to IL-4, suggests that the amino acid residues against which the antibodies are directed may be exposed on the surface of IL-4.

Monoclonal Anti-polypeptide Antibodies

Monoclonal antibodies were prepared essentially as described by Kohler and Milstein [Nature 256:495 (1975)]. All incubations were carried out at 37° C. in a 5% CO$_2$ incubator.

Balb/c mice (Charles River) were immunologically sensitized by administering 500 μl of 2,6,10,14-Tetramethylpentadecane (Pristane) intraperitoneally (i.p.). About four days later, 250 μg of polypeptide No. 7 (Table 1; corresponding to residues 61–82 of human IL-4) were dissolved in 250 μl volumes of phosphate buffered saline (PBS), 250 μl aliquots of Freund's complete adjuvant were added, and the mixtures were homogenized and administered i.p. to each mouse. About one month later, booster injections containing 125 μg of the polypeptide in 1:1 diluted Freund's incomplete adjuvant were administered i.p.

Three or four weeks later, final i.p. injections of 250 μg of polypeptide No. 7 in PBS were administered. Periodically during the course of immunization, test bleeds were made from the tail veins and analyzed by ELISA as described above. Four days after the final immunizations, the animals were sacrificed and their spleens were removed.

The spleens were macerated between two slides in fresh RPMI 1640 medium containing 100 μg/ml streptomycin and 100 units/ml penicillin (RPMI pen/strep medium) and then transferred to a large tube. After allowing debris to settle for 1 minute, cells in the upper layer of the tube were transferred to a 5 ml tube. Four milliliters of the RPMI pen/strep medium were added and the cells were suspended and then sedimented by centrifugation at about 300×g for 8 minutes.

A 5:1 ratio of spleen cells to NS-1 mouse myeloma cells (ATCC TIB 18) was prepared and washed once with the RPMI pen/strep medium. After pelleting the cells as before and discarding the medium, 0.5 ml of PEG (2 g per liter in 75 mM HEPES buffer) having a molecular weight of about 1500 daltons was added dropwise over a period of 1 minute at 37° C., with gentle agitation every 20 seconds. The PEG addition was repeated, first with 0.5 and then 1.0 ml of the PEG solution.

Following fusion, the cells were sedimented and washed for 1 minute periods with 0.5, 1.0, 2.0, 4.0, 8.0, 16.0 and 32.0 ml of the RPMI pen/strep medium. The fusion cells were sedimented as before and the medium was discarded, after which about 1×10$^5$ spleen cells from a naive mouse were added as feeder cells in RPMI pen/strep medium containing 0.2933 mg/ml glutamine and 10% fetal calf serum (FCS) and the cells were mixed and then sedimented as before. After isolation from the mouse the day before, the feeder splenocytes had been incubated overnight at 37° C. in RPMI pen/strep medium containing the glutamine and FCS.

The fusion and feeder cells were grown together for 7 days in RPMI pen/strep medium containing 0.2933 mg/ml glutamine, 10% FCS, $1\times10^{-2}$ M hypoxanthine, $4\times10^{-5}$ M aminopterin and $1.6\times10^{-3}$ M thymidine (HAT medium) in 96-well flat-bottom microtiter plates (COSTAR), 150 μl per well. After this incubation period, the medium in each well was replaced with HT medium (HAT medium lacking aminopterin) and incubation was continued.

After several days, ELISA was carried out on the hybridoma supernatants as described above, except that a labeled anti-mouse IgG antibody was used. Hybridomas in wells testing positive were cloned by limiting dilution in HT medium.

A total of 382 cloned hybridomas were produced in this way, all of which produced monoclonal antibodies. After screening these hybridomas by ELISA using polypeptide No. 7 as the antigen, 12 positive cell lines were identified. Of these, 10 were found positive by ELISA screening against IL-4.

Ouchterlony screening of 8 of the positive clones in agar carried out by standard methods with immunoglobulin-specific antisera showed that 6 of the clones produced IgG1, one produced IgG2a and one produced IgM antibodies.

Preparation of Anti-Idiotypic Antibodies

To produce anti-idiotypic antibodies, 1.5 mg of the antiserum 343-6 IgG fraction described above in 0.5 ml of phosphate-buffered saline were added to 0.5 ml of Freund's complete adjuvant and mixed thoroughly to form an emulsion. The sample was injected subcutaneously into a sheep (Dorset crossbreed). Booster vaccinations were administered at several-week intervals thereafter in an identical manner, except that Freund's incomplete adjuvant was used.

Occasional blood samples taken during the course of immunization were subjected to ELISA analysis using the antiserum 343-6 IgG fraction as the antigen as described above, except that blocking with immunoglobulin was omitted and 5.0 ng of horseradish peroxidase-labeled donkey anti-sheep IgG was used as the second antibody. The sheep antiserum thus obtained (designated antiserum 1448) was found to specifically bind to the rabbit antiserum 343-6 IgG fraction but not to IL-4 or to polypeptide No. 7.

To determine whether sheep antiserum 1448 did indeed contain anti-idiotypic antibodies, a serial dilution of the antiserum was subjected to radioligand receptor binding analysis using $^{125}$I-IL-4 and Daudi cells as described above, with the results shown in FIG. 4. Each sample in the assay contained $2\times10^6$ cells and 50 pM of $^{125}$I-IL-4 ($2\times10^5$ cpm). Specific binding in the absence of antiserum was 5,931 cpm.

Figure 4:
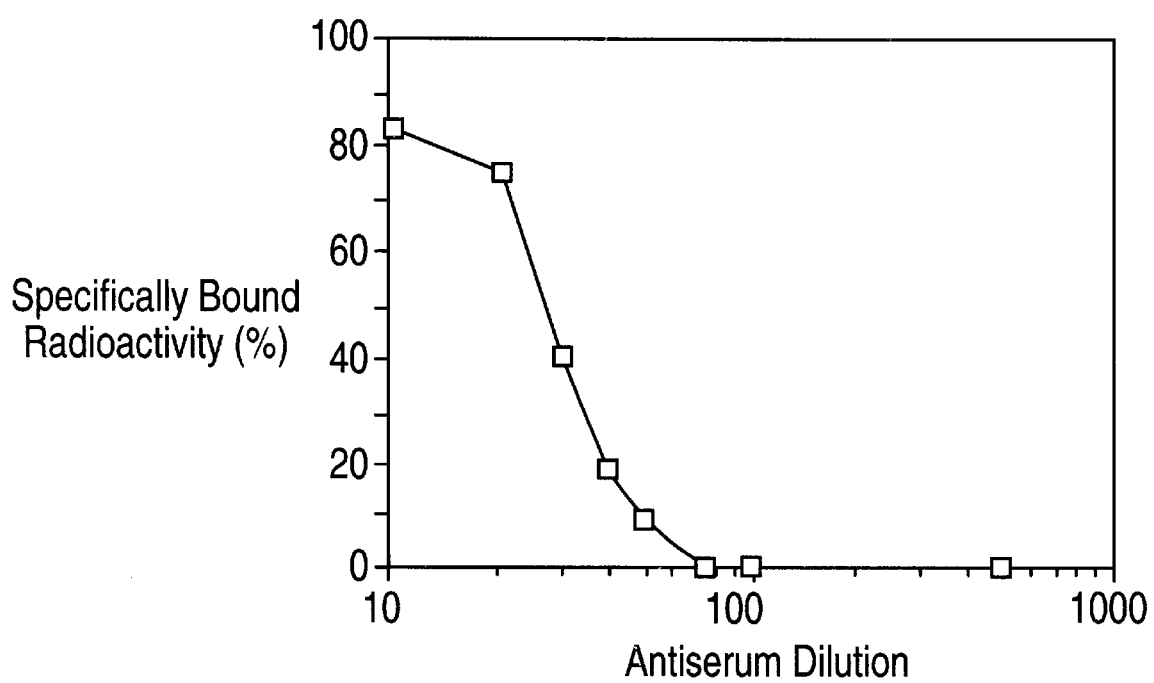
FIG. 4 is a graphical representation of the inhibition of the specific binding of $^{125}$I-IL-4 to Daudi cells by anti-idiotypic antiserum 1448, showing % inhibition of specifically bound radioactivity as a function of decreasing antiserum concentration.

As shown in FIG. 4, sheep antiserum 1448 was a strong competitive inhibitor of the binding of the labeled IL-4 to the cells, abolishing more than 80% of the specific binding at the lower dilutions. In contrast, sheep pre-immune serum had no effect on the binding of the IL-4.

Epitope Analysis

To determine which amino acid residues in polypeptides Nos. 6 and 7 were critical to the production of antibodies which could inhibit the binding of IL-4 to cellular receptors, epitope analysis was carried out essentially as described by Geysen et al., [Proc. Natl. Acad. Sci. USA 81:3998 (1984)].

The method of Geysen et al. allows the rapid concurrent synthesis on solid supports of hundreds of small polypeptides of sufficient purity and in sufficient quantity to carry out ELISA, while the polypeptides are still attached to the solid supports on which they were synthesized. In principle, ELISA is carried out on such polypeptides using antibodies which had been prepared against a larger polypeptide or protein having an amino acid sequence which includes the sequences of the small polypeptides. If the antibodies are specific for an epitope within the larger immunogen that is encompassed by the small synthetic polypeptides, the antibodies will bind to the polypeptides and can be detected by ELISA.

Using the method of Geysen al., supra, a series of 15 octapeptides was synthesized on polyethylene pins (Cambridge Research Biochemicals, Inc., Valley Stream, N.Y.), the amino acid sequences of which, in the aggregate, spanned all of the residues in polypetide No. 7 (corresponding to residues 61–82 of mature human IL-4). The sequences of these octapeptides are shown in Table 3.

TABLE 3

Octapeptides Based Upon
Residues 61–82 of Mature Human IL-4

| SEQ. ID. NO. | Octapeptide No. | Sequence | Corresponding IL-4 Residues | Center* Residue |
| --- | --- | --- | --- | --- |
| 13 | 1 | KDTRCLGA | 61–68 | 65 |
| 14 | 2 | DTRCLGAT | 62–69 | 66 |
| 15 | 3 | TRCLGATA | 63–70 | 67 |
| 16 | 4 | RCLGATAQ | 64–71 | 68 |
| 17 | 5 | CLGATAQQ | 65–72 | 69 |
| 18 | 6 | LGATAQQF | 66–73 | 70 |
| 19 | 7 | GATAQQFH | 67–74 | 71 |
| 20 | 8 | ATAQQFHR | 68–75 | 72 |
| 21 | 9 | TAQQFHRH | 69–76 | 73 |
| 22 | 10 | AQQFHRHK | 70–77 | 74 |
| 23 | 11 | QQFHRHKQ | 71–78 | 75 |
| 24 | 12 | QFHRHKQL | 72–79 | 76 |
| 25 | 13 | FHRHKQLI | 73–80 | 77 |
| 26 | 14 | HRHKQLIR | 74–81 | 78 |
| 27 | 15 | RHKQLIRF | 75–82 | 79 |

*The center residues of the octapeptides were arbitrarily designated by adding four to the residue position in mature human IL-4, to which the N-terminal residue of each octapeptide corresponded.

In like fashion, a series of 17 pin-immobilized octapeptides together spanned all of the residues corresponding to residues 47–79 mature human IL-4 was prepared. The amino acid sequences octapeptides are shown in Table 4.

TABLE 4

Octapeptides Based Upon
Residues 47–70 of Mature Human IL-4

| SEQ. ID. NO. | Octapeptide No. | Sequence | Corresponding IL-4 Residues | Center* Residue |
|---|---|---|---|---|
| 28 | 1 | RAATVLRQ | 47–54 | 51 |
| 29 | 2 | AATVLRQF | 48–55 | 52 |
| 30 | 3 | ATVLRQFY | 49–56 | 53 |
| 31 | 4 | TVLRQFYS | 50–57 | 54 |
| 32 | 5 | VLRQFYSH | 51–58 | 55 |
| 33 | 6 | LRQFYSHH | 52–59 | 56 |
| 34 | 7 | RQFYSHHE | 53–60 | 57 |
| 35 | 8 | QFYSHHEK | 54–61 | 58 |
| 36 | 9 | FYSHHEKD | 55–62 | 59 |
| 37 | 10 | YSHHEKDT | 56–63 | 60 |
| 38 | 11 | SHHEKDTR | 57–64 | 61 |
| 39 | 12 | HHEKDTRC | 58–65 | 62 |
| 40 | 13 | HEKDTRCL | 59–66 | 63 |
| 41 | 14 | EKDTRCLG | 60–67 | 64 |
| 42 | 15 | KDTRCLGA | 61–68 | 65 |
| 43 | 16 | DTRCLGAT | 62–69 | 66 |
| 44 | 17 | TRCLGATA | 63–70 | 67 |

*The center residues of the octapeptides were arbitrarily designated by adding four to the residue position in mature human IL-4, to which the N-terminal residue of each octapeptide corresponded.

To carry out epitope analysis on polypeptide No. 7, antiserum designated 129-88 from a rabbit immunized with the polypeptide as described above was subjected to ELISA, using the polyethylene pin-immobilized octapeptides shown in Table 3 as the antigen. This antiserum was found to strongly inhibit the binding of $^{125}$I-IL-4 to Daudi cells, in an assay performed as described above. The ELISA was carried out on antiserum 129-88 essentially as described above in 96-well microtiter plates, except that the pins were used in the wells instead of coating free antigen onto the wells. Prior to reading the color development using a Titertek MCC 340 ELISA plate reader, the pins were removed from the walls.

Figure 5:
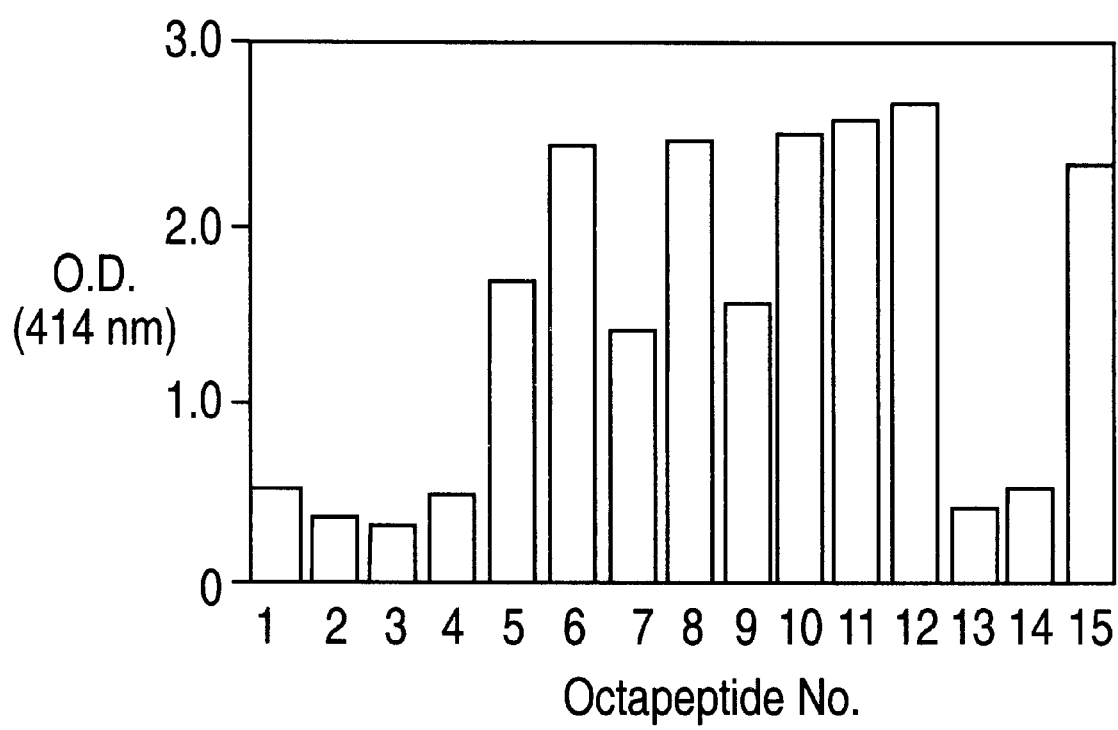
FIG. 5 is a graphical representation of the results of epitope analysis performed on rabbit antiserum against polypeptide No. 7. ELISA absorbance produced by binding of the antiserum to a series of octapeptides used in the analysis is shown. The numbers of the octapeptides correspond to the numbers in Table 3.

The results of this analysis is shown in FIG. 5, where absorbance at 414 nm is shown for each of the octapeptides. The numbers of the octapeptides shown in FIG. 5 correspond to the numbers in Table 3. Strong binding of antibodies to octapeptides 5–12 can be seen in FIG. 5. Referring to Table 3, it can be seen that the approximate centers of these octapeptides corresponded to residues 69–76 of mature human IL-4. These data, combined with the fact that antiserum 129-88 inhibited the binding of the labeled IL-4 to the cellular receptors, suggests that residues 69–76 of mature human IL-4 constitute an epitope(s), antibodies against which inhibit the binding of human IL-4 to cellular receptors.

Figure 6A:
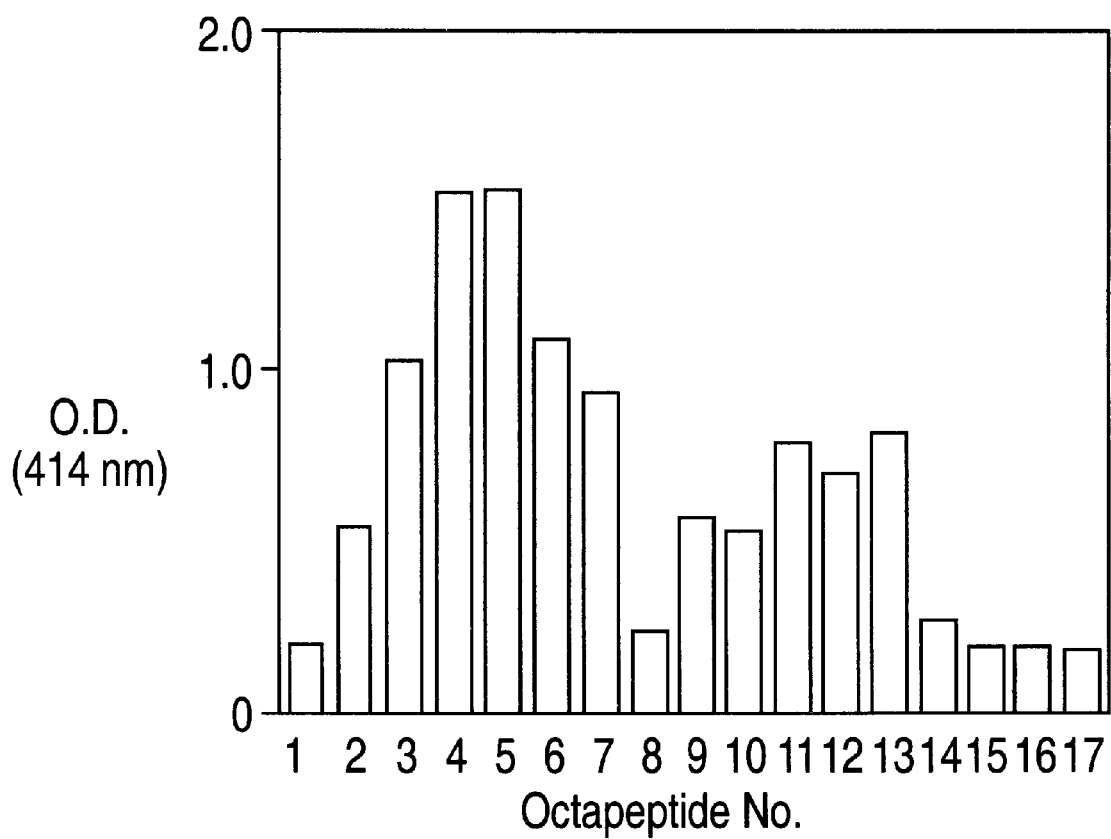
FIG. 6 is a graphical representation of the results of epitope analysis performed on rabbit antiserum against polypeptide No. 6. ELISA absorbance produced by binding of the antiserum to a series of octapeptides used in the analysis is shown. The antiserum used to obtain the results shown in panel A was collected early in the course of immunization of the rabbit and did not inhibit the binding of $^{125}$I-IL-4 to Daudi cells. The antiserum used in panel B was collected later and was a strong inhibitor of the binding of the labeled IL-4. The numbers of the octapeptides correspond to the numbers in Table 4.
Figure 6B:
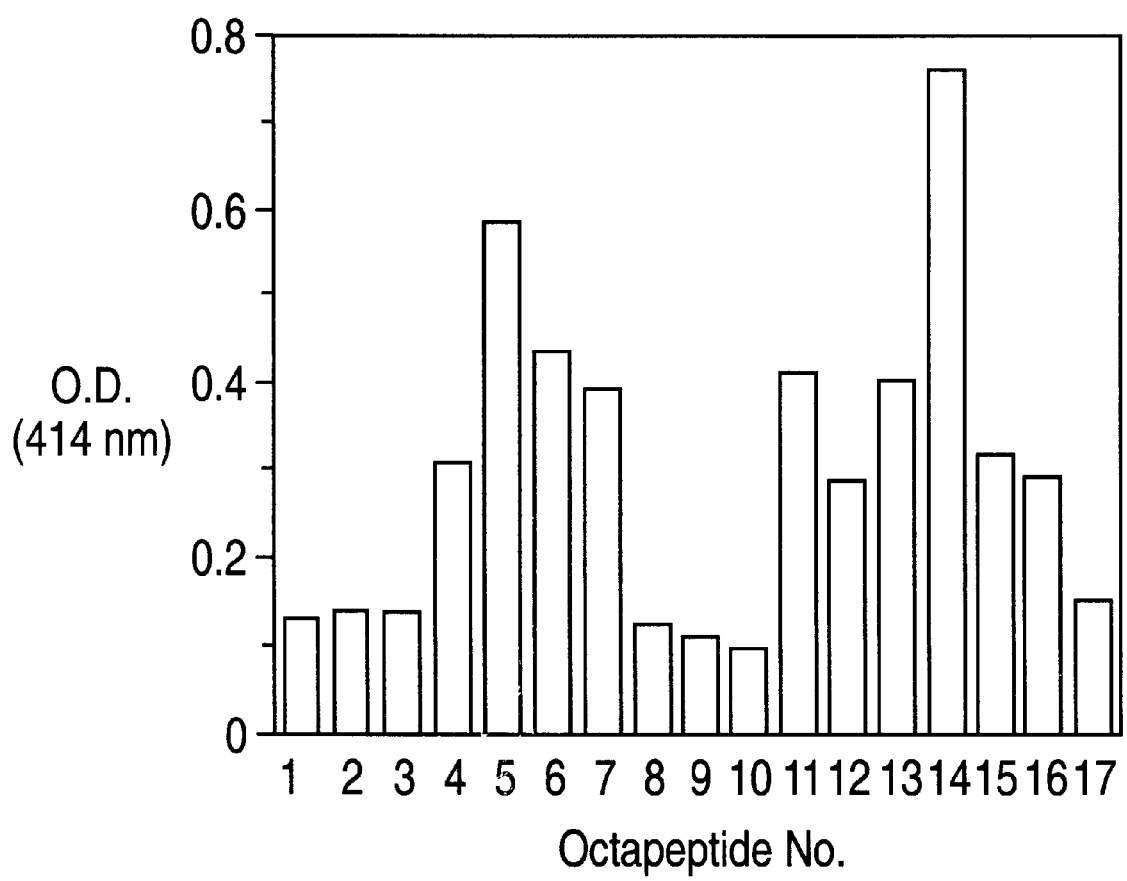

In a similar fashion, the immobilized octapeptides shown in Table 4 were used to analyze rabbit antiserum produced against polypeptide No. 6. This antiserum, designated 342-6, was evaluated twice for ability to inhibit the binding of $^{125}$-I-IL-4 to Daudi cells. Serum samples prepared early in the course of immunization (early antiserum 342-6) did not inhibit labeled IL-4 binding; samples prepared later (late antiserum 342-6) were strongly inhibitory. The results of these analyses are shown in FIG. 6A and B for the early and late antiserum, respectively. The numbers of the octapeptides shown in FIG. 6 correspond to the numbers in Table 4.

As shown in FIG. 6A, the non-inhibitory early antiserum 342-6 against polypeptide No. 6 contained antibodies reactive with octapeptides 3–7 and 9–13. Referring to Table 4, it can be seen that the centers of these octapeptides corresponded approximately to residues 53–57 and 59–63, respectively, of mature human IL-4.

The late, inhibitory antiserum 342-6 produced a similar binding pattern (FIG. 6B), except that it also contained antibodies which exhibited stronger binding to octapeptides 11–16, the centers of which corresponded to residues 61–66 of the human IL-4. The data of panels A and B of FIG. 6, taken together, suggest that residues 61–66 of mature human IL-4 constitute an epitope, antibodies against which inhibit the binding of human IL-4 to cellular receptors.

This suggestion is strengthened by ELISA studies carried out as described above using polypeptides Nos. 6 and 7 and one of the monoclonal antibodies against polypeptide No. 7. This antibody bound strongly to both of the polypeptides. It also strongly inhibited the binding of $^{125}$I-IL-4 to Daudi cells. The only common subsequence in the polypeptides is KDTRC (SEQ.ID.NO.: 45), which corresponds to residues 61–65 of mature human IL-4. It follows that this inhibitory monoclonal antibody must have been directed against this subsequence, and the subsequence must constitute an important epitope.

Many modifications and variations of this invention may be made without departing from its spirit and scope, as will become apparent to those skilled in the art. The specific embodiments described herein are offered by way of example only, and the invention is to be limited only by the terms of the appended claims.

What is claimed is:

1. A method for producing antibodies which specifically bind to and inhibit the binding of human Interleukin-4 (IL-4) to receptors comprising administering to an animal a sufficient quantity of a polypeptide consisting of amino acid residues 61 to 82 of IL-4, (SEQ.ID.NO.:7), wherein the animal produces antibodies against the polypeptide, said antibodies being able to specifically bind to human IL-4 and are able to inhibit the binding of human IL-4 to cellular receptors.

2. The method of claim 1 wherein the antibodies are polyclonal obtained from serum of the animal.

3. The method of claim 1 wherein the antibodies are monoclonal produced by a hybridoma cell line, said hybridoma cell line having been obtained from an antibody secreting somatic cell of the animal which has been fused to a myeloma cell.

* * * * *